United States Patent [19]

Fujisaki et al.

[11] Patent Number: 4,820,841
[45] Date of Patent: Apr. 11, 1989

[54] CHROMOGENIC QUINOLINE COMPOUNDS

[75] Inventors: Hideaki Fujisaki, Kyoto; Kouzou Mizuno, Uji; Yukihiko Sueto; Katsuhiko Tsunemitsu, both of Kyoto, all of Japan

[73] Assignee: Yamada Chemical Co., Ltd., Kyoto, Japan

[21] Appl. No.: 900,771

[22] Filed: Aug. 26, 1986

Related U.S. Application Data

[63] Continuation-in-part of Ser. No. 580,604, Feb. 16, 1984, Pat. No. 4,598,150.

[30] Foreign Application Priority Data

Feb. 16, 1983 [JP] Japan .................. 58-27142

[51] Int. Cl.⁴ .................. C07D 215/12; C07D 215/18; C07D 215/20
[52] U.S. Cl. .................. 546/152; 546/178; 546/180
[58] Field of Search .................. 546/178, 152

[56] References Cited

U.S. PATENT DOCUMENTS 4,287,335  9/1981  Ichimura .................. 542/455

FOREIGN PATENT DOCUMENTS 3219239  5/1982  Fed. Rep. of Germany .
21033  12/1966  Japan .
27169  8/1976  Japan .
58-25317  12/1983  Japan .
2136823  9/1984  United Kingdom .

OTHER PUBLICATIONS

Beilsteins Handbuch Der Organischen Chemie, Zwanzigster Band, pp. 500 and 501.
Beilsteins Handbuch Der Organischen Chemie, Einundzwanzigster Band, pp. 149 and 193.
Beilsteins Handbuch Der Organischen Chemie, Zweites Erganzungswerk, Einundzwanzigster Band, pp. 94, 151, 152 and 173.
J. of Heterocyclic Chemistry, 9 (4), pp. 789-799 (1972).
J. of Indian Chemical Society, 49 (2), pp. 139-144 (1972).

Primary Examiner—Glennon H. Hollrah
Assistant Examiner—D. B. Springer
Attorney, Agent, or Firm—Cushman, Darby & Cushman

[57] ABSTRACT

Disclosed herein is a novel chromogenic compound of the formula:

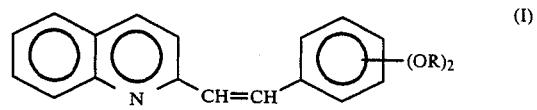

wherein R represents an alkyl group of 6 to 12 carbon atoms or benzyl group, and ring A and ring B in the quinolyl group may be substituted, a color forming composition containing said chromogenic compound, and pressure- or heat-sensitive recording paper based on said color forming composition.

2 Claims, 4 Drawing Sheets

CHROMOGENIC QUINOLINE COMPOUNDS

This application is a continuation-in-part of Ser. No. 580,604, filed 02-16-84, now U.S. Pat. No. 4,598,150.

BACKGROUND OF THE INVENTION

The present invention relates to a novel chromogenic compound, color developing composition containing the same suitable for recording paper, and pressure- or heat-sensitive recording paper coated with microcapsules containing the color developing composition.

Heretofore, a variety of yellow color forming agents have been proposed and they are broadly clasified into the following two groups.

Group I: Those having a lactone ring in the molecule.

(i) Fluoran derivatives such as 3,6-dialkoxyfluoran (refer to Japanese Patent Publication Nos. 45-4698 (1970) and 46-16053 (1971)) and 3-N-alkylaminofluoran (refer to Japanese Patent Publication Nos. 46-22650 (1971) and 48-4051 (1973)).

(ii) Chromenopyrazole compounds (refer to Japanese Patent Publication No. 46-23513 (1971)).

(iii) Aminophthalide compounds (refer to Japanese Patent Application Laying-Open (KOKAI) No. 54-111528 (1979)).

(iv) Acyloxytetrachlorophthalide compounds (refer to Japanee Patent Publication No. 45-25654 (1970)).

Group II: Those having no lactone ring in the molecule.

(i) Spiropyran derivatives (refer to Japanese Patent Publication Nos. 46-10075 (1971) and 46-11113 (1971)).

(ii) Styryl compounds (refer to Japanese Patent Publication Nos. 41-21033 (1966) and 51-27169 (1976)).

(iii) Pyridine derivatives (refer to Japanese Patent Publication No. 53-9127 (1978)).

(iv) Monomethine compounds (refer to Japanese Patent Application Laying-Open (KOKAI) No. 52-23406 (1977) and Japanese Patent Publication No. 49-5929 (1974)).

(v) Benzopyran compounds (refer to Japanese Patent Publication No. 56-19274 (1981)).

The compounds belonging to Group I which have a lactone ring in the molecule have an advantage of being less liable to spontaneous color formation in case of coating the solution thereof with a paper and being readily soluble in solvents. However, they also have a disadvantage of giving rise to a color image which is poor in color density and light-fastness.

On the other hand, the compounds belonging to Group II which have no lactone ring in the molecule have an advantage of producing a color image which is good in color density and light-fastness. However, they also have a disadvantage of being poor in solubility, being liable to spontaneous color formation in case of contact with paper, and being readily lost by sublimation.

Previously to the present invention, two of the present inventors as a part of inventors completed an invention relating to:

(1) a chromogenic compound of the formula

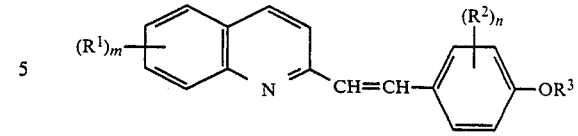

wherein $R^1$ and $R^2$ independently represent a hydrogen atom, lower alkyl group of 1 to 5 carbon atoms, lower alkoxy group of 1 to 5 carbon atoms, or halogen atom; $R^3$ represents a hydrogen atom, alkyl group of 1 to 12 carbon atoms, alkoxyalkyl group of 1 to 12 carbon atoms, halogenoalkyl group of 1 to 12 carbon atoms, phenyl group which may be substituted, or benzyl group which may be substituted; and m and n are an integer of 1 or 2; providing that $R^1$ and $R^2$ do not represent a hydrogen atom, methyl group, and methoxy group when $R^3$ represents a hydrogen atom or methyl group;

(2) a color forming composition for a recording material, comprising at least one chromogenic compound as defined above which is capable of developing a color upon contact with an electron acceptor; and (3) pressure- or heat-sensitive recording paper comprising microcapsules containing at least one chromogenic compound as defined above, said chromogenic compound functioning as a color former and being dissolved in an organic solvent in said microcapsules (Refer to G.B. Pat. No. 2136823A and U.S. patent application No. 580,604 filed on Feb. 16, 1984.).

The present inventors carried out studies for obtaining a new chromogenic compound which is easier to synthesize and more soluble than the one disclosed in the previous publications mentioned above, and as a result, it is found that a chromogenic compound of the formula (I):

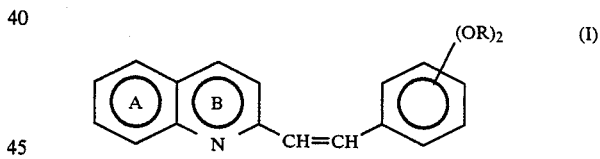

wherein R represents an alkyl group of 6 to 12 carbon atoms or benzyl group, and ring A and ring B in the quinolyl group may be substituted is easy to synthesize, is readily soluble, and stable to light, and in addition, develops a color image of deep hue. On the basis of the findings the present invention has been attained.

SUMMARY OF THE INVENTION

In the first aspect of the present invention, there is provided a chromogenic compound represented by the formula (I):

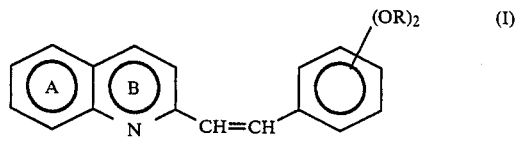

wherein R represents an alkyl group of 6 to 12 carbon atoms or benzyl group, and ring A and ring B in the quinolyl group may be substituted.

In the second aspect of the present invention, there is provided a color forming composition for recording paper, comprising at least one chromogenic compound as a color former represented by the formula (I):

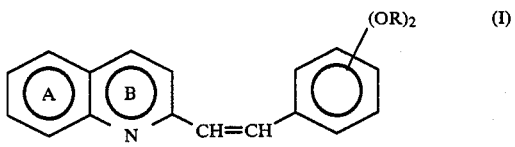

and an organic solvent for a chromogenic compound.

In the third aspect of the present invention, there is provided a pressure- or heat-sensitive recording paper produced by coating a paper with microcapsules containing at least one chromogenic compound represented by the formula (I):

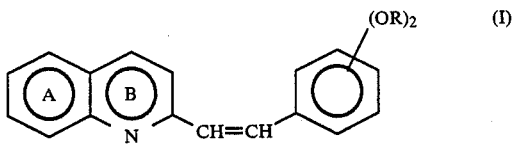

said chromogenic compound as a color former being dissolved in an organic solvent in the microcapsules.

BRIEF DESCRIPTION OF THE DRAWINGS

Of the attached drawings, FIGS. 1 to 4 respectively shows the infrared absorption spectra of the chromogenic compounds respectively produced in Examples 1, 2, 3 and 6.

DETAILED DESCRIPTION OF THE INVENTION

Figure 1:
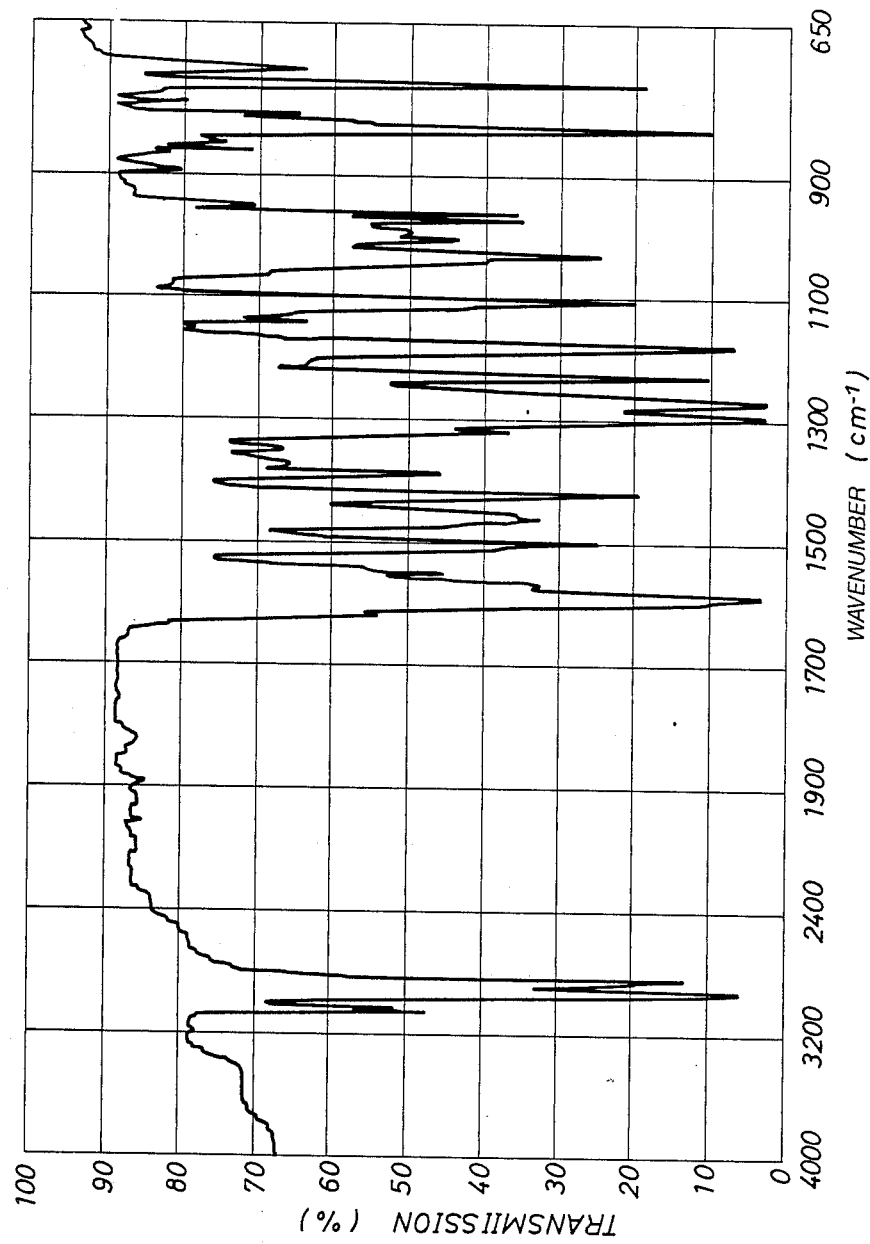

The present invention relates to a chromogenic compound represented by the formula (I) below, a color developing composition containing the chromogenic compound as a color former, and a pressure- or heat-sensitive recording paper coated with microcapsules containing the color forming composition.

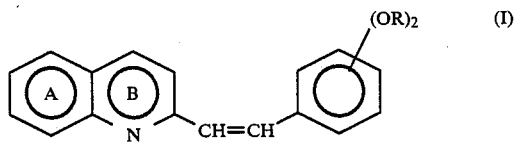

wherein R represents an alkyl group of 6 to 12 carbon atoms or benzyl group, and ring A and ring B in the quinolyl group may be substituted.

The chromogenic compound of the present invention has the following features. It has a lower melting point that the compound disclosed in G.B. No. 2136823A and is readily soluble in a cheap solvent among solvents used for pressure- or heat-sensitive recording paper, if the hydrocarbon residue (R) in the formula (I) has 6 or more carbon atoms. In addition, it is more stable to light when in the form of solution and it produces a color image of deep hue, if one of the two —OR groups on the styryl group is at the ortho position with respect to the ethylenic bond. (Incidentally, a styryl quinoline compound in the form of solution gradually loses its color forming ability in proportion to the amount of light to which it is exposed, because the double bond of the styryl group contained therein undergoes chemical reactions (presumably dimerization) upon exposure to light.) With the chromogenic compound of the present invention, this disadvantage is eliminated if one —OR group occupies at the ortho position with respect to the ethylenic bond. Further, the chromogenic compound of the present invention is readily desensitized by an desensitizing ink.

The chromogenic compound of the present invention can be produced by the condensation of a quinaldine derivative (II) and a substituted benzaldehyde (III) as shown below. The condensation is promoted in the presence of a dehydrating agent.

(First process)

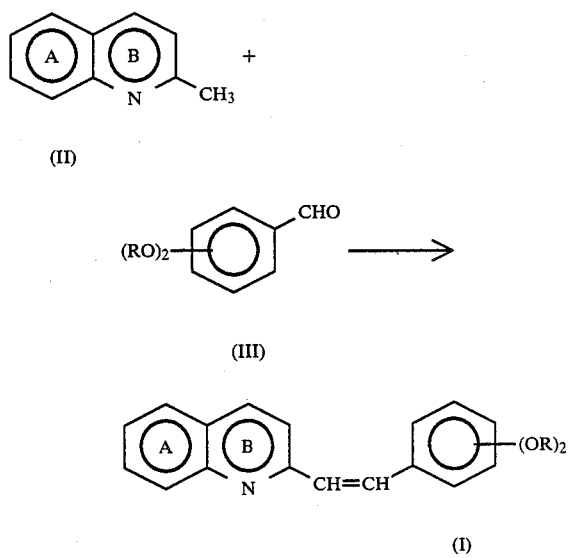

Alternatively, it can be produced by condensing a quinaldeine derivative (II) and a dihydroxybenzaldehyde (IV) to form a dihydroxystyrylquinoline (V), followed by alkylation with a proper alkylating agent (VI) (e.g., an alkyl halide), as shown below.

(Second process)

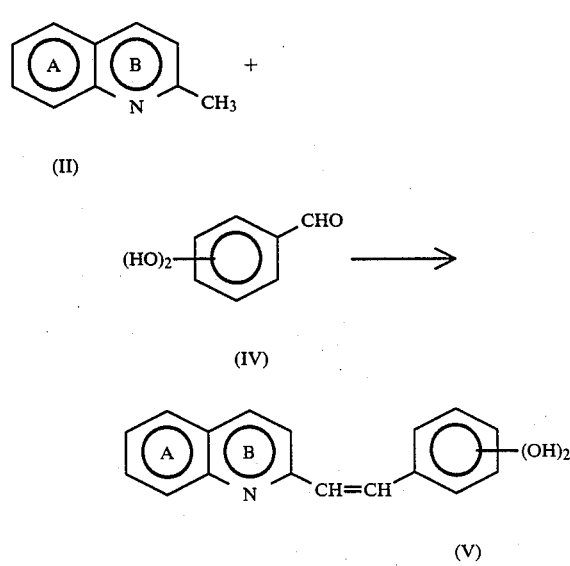

(V)

$$2RX \longrightarrow$$

(VI)

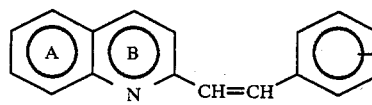

(I)

As compared with the first process, the second one is faster in condensation reaction and higher in yields.

The chromogenic compound of the present invention is almost colorless but it rapidly changes into yellow upon contact with an electron acceptor. Therefore, it is useful as a color developing agent for pressure- or heat-sensitive recording paper (copying paper).

The chromogenic compound of the present invention is superior to conventional yellow color developing agents in the following points.

(1) It produces an image of higher color density, and it is stabler to light.
(2) It is more soluble in organic solvents.
(3) It is less liable to spontaneous color formation in case of coating the solution thereof with a paper.
(4) It is less liable to loss by sublimation.
(5) It is more easily desensitized with an antisensitive ink.

As Table 1 shows, the chromogenic compound of the present invention is superior in color density of the image, light-fastness of the image, and desensitization to the comparative compounds disclosed in G.B. No. 2136823A.

TABLE 1

|  |  | Color density | desensitization |
|---|---|---|---|
| The present invention |  |  |  |
| Compound No. 1 | 1-(2,4-dioctyloxyphenyl)-2-(2'-quinolyl)ethylene | 0.96 | 0.23 |
| Compound No. 3 | 1-(2,4-didodecyloxyphenyl)-2-(2'-quinolyl)ethylene | 0.79 | 0.16 |
| GB 2136823A |  |  |  |
| Compound No. 13 | 1-(3-methoxy)-4-octyloxyphenyl)-2-(2'-quinolyl)ethylene | 0.77 | 0.56 |
| Compound No. 14 | 1-(3-methoxy)-4-dodecyloxyphenyl)-2-(2'-quinolyl)ethylene | 0.72 | 0.48 |

The present invention:

Compound No. 1:

Compound No. 3:

GB 2136823A:

Compound No. 13:

Compound No. 14:

The color density and desensitization are measured by the following methods.

(1) Color Density

A sheet of base paper is coated by doctor knife with a 3% solution of sample compound in KMC (alkylnaphthalene solvent for pressure-sensitive recording paper, made by Kureha Chemical Industry Co., Ltd., Japan) at a coating weight of 5 g/m². With the coated paper placed on a color-developer sheet (clay-coated paper), pressure is applied by rolling to effect color formation. Thirty seconds after color formation, the color density is determined according to the amount of light absorbed by the color which is measured by using an integrating type spectrophotometer (Model UV-200, made by Shimadzu Seisakusho Ltd., Japan).

(2) Desensitization

At first, coated-front sheet (clay-coated paper) is coated with a desensitizing ink composed mainly of polypropylene glycol having an average molecular weight of about 3000 at a coating weight of 2 to 3 g/m². On the other hand, coated-back sheet is prepared by coating with microcapsules containing 3 parts by weight of the chromogenic compound and 97 parts by weight of KMC (alkylnaphthalene solvent for pressure-sensitive recording paper, made by Kureha Chemical Industry Co., Ltd.) according to the method described in Example 9. With the coated-back sheet placed on the coated-front sheet, the microcapsules are broken by pressure rolling. Three days later, the color density on the coated-front sheet is determined in terms of Macbeth reflection density. For reference, the same procedure as above is repeated except that no desensitizing ink is used. Desensitization is expressed in relative value and the recording paper having the relative value of not more than 0.25 is used in practical.

The chromogenic compound of the present invention can be encapsulated into microcapsules for pressure-sensitive recording paper by any known process. For example, microencapsulation by coacervation as disclosed in U.S. Pat. Nos. 2,806,457 and 2,800,458 may be adopted. The other suitable process is disclosed in Japanese Patent Publication No. 45-14039 (1970).

The microcapsules containing the chromogenic compound of the present invention may be coated onto either a supporting paper or a paper coated with electron acceptor. In the former case two pieces of paper, one coated with microcapsules and the other coated with an electron acceptor, are required for color formation, and in the latter case the color formation is accomplished on a single piece of paper.

Upon application of pressure in use of the pressure-sensitive recording paper, the microcapsules are broken and the chromogenic compound contained therein comes into contact with the adjacent electron acceptor to effect color formation. The electron acceptor may be on the same paper as for the microcapsules or on the paper separate from the one coated with the microcapsules.

As an electron acceptor, organic acids, acid clay, activated clay, phenol-formaldehyde resin, metal salts of aromatic carboxylic acids, and aromatic hydroxy compounds such as bisphenol A may be exemplified.

As a wall material of microcapsules, polyvinyl alcohol, polyacrylic acid, hydroxyethyl cellulose, methyl cellulose, carboxymethyl cellulose, polyacrylamide, polyvinyl pyrrolidone, gelatin, and starch may be exemplified.

Preferable chromogenic compounds of the present invention are
1-(2,4-dioctyloxyphenyl)-2-(2'-quinolyl)ethylene,
1-(2,4-dibenzyloxyphenyl)-2-(2'-quinolyl)ethylene,
1-(2,4-didodecyloxyphenyl)-2-(2'-quinolyl)ethylene,
1-(4,5-didodecyloxyphenyl)-2-(6'-ethoxy-2'-quinolyl)ethylene,
1-(4,5-dibenzyloxyphenyl)-2-(6'-ethoxy-2'-quinolyl)ethylene,
1-(5,6-dioctyloxyphenyl)-2-(2'-quinolyl)ethylene,
1-(2,4-dioctyloxyphenyl)-2-(6'-chloro-2'-quinolyl)ethylene, and
1-(2,4-dioctyloxyphenyl)-2-(6'-methyl-2'-quinolyl)ethylene.

Most suitable among them is
1-(2,4-dioctyloxyphenyl)-2-(2'-quinolyl)ethylene.

The chromogenic compound of the present invention is highly soluble, stable to light, capable of forming color images of deep hue, and readily desensitized.

The present invention will be explained in more detail with reference to the following non-limitative examples.

EXAMPLE 1

Synthesis of
1-(2,4-dioctoxyphenyl)-2-(2'-quinolyl)ethylene
(Compound No. 1)

14.3 g of quinaldine, 13.8 g of 2,4-dihydroxybenzaldehyde, and 30 ml of acetic anhydride were reacted under reflux for 2 hours. The reaction product was added to 200 ml of water. After stirring for a while, the resulting precipitates were filtered out, washed, and dried, and then 24 g of slightly yellowish crystals having a melting point of 126 to 133.5° C. was obtained. This compound was identified as 1-(2,4-diacetoxyphenyl)-2-(2'-quinolyl)ethylene of the following structural formula.

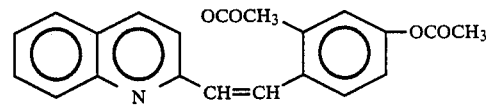

34.7 g of this compound was reacted with 48.2 g of n-octyl bromide and 33.1 g of anhydrous potassium carbonate in 60 ml of diethylene glycol monomethyl ether at 140° C. for 2 hours. After cooling, the reaction product was filtered out and washed. The pastelike reaction product was dispersed into 200 ml of water. The dispersed particles were filtered out, washed, and dried, and then 40 g of grayish white crystals having a melting point of 51° to 54.3° C. were obtained. This compound was identified as 1-(2,4-dioctoxyphenyl)-2-(2'-quinolyl)ethylene of the following structural formula.

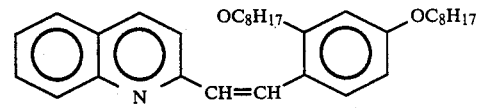

When dissolved in 95% acetic acid, this compound gave the $\lambda_{max}$ at 433 nm. A toluene solution of this compound was colorless, but it formed a color giving the $\lambda_{max}$ at 455 nm on the clay-coating paper of pressure-sensitive recording paper. This color was nearly orange.

The results of elemental analysis were as follows:

|  | C(%) | H(%) | N(%) |
| --- | --- | --- | --- |
| calcd. for $C_{33}H_{45}NO_2$: | 81.13 | 9.24 | 2.87 |
| Found: | 81.44 | 9.39 | 2.85 |

The infrared spectrum of Compound No. 1 is shown in FIG. 1.

EXAMPLES 2 to 8

The same procedure as in Example 1 was repeated except that quinaldines, dihydroxybenzaldehydes, and nalogenated hydrocarbons as shown in Table 2 were used, and chromogenic compounds as shown in Table 2 were obtained.

All of them were colorless in toluene solution but formed a yellow color upon reaction with an eletron acceptor. The chromogenic compounds obtained in Examples 2 and 3 remarkably formed a color image of deep hue on the clay coating paper.

TABLE 23

Figure 2:
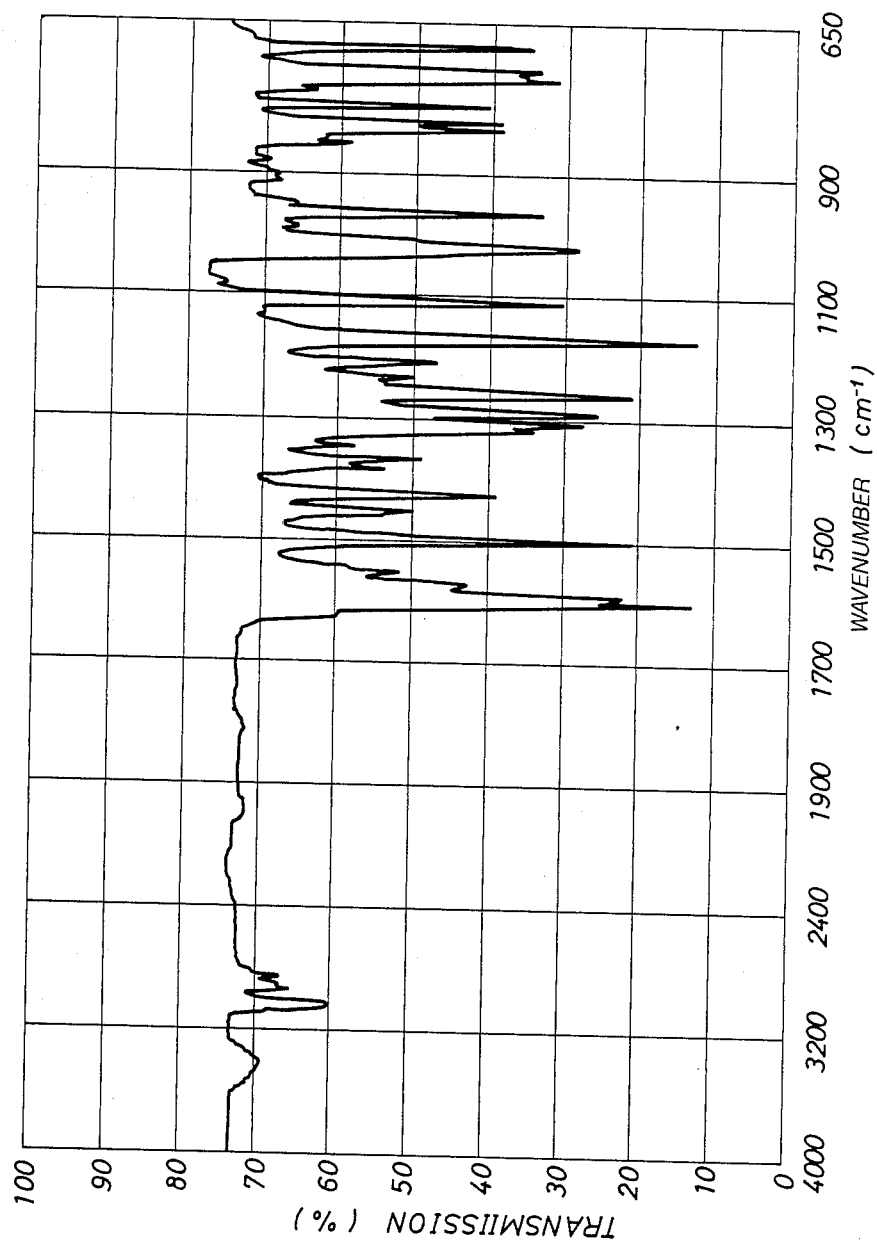
Figure 3:
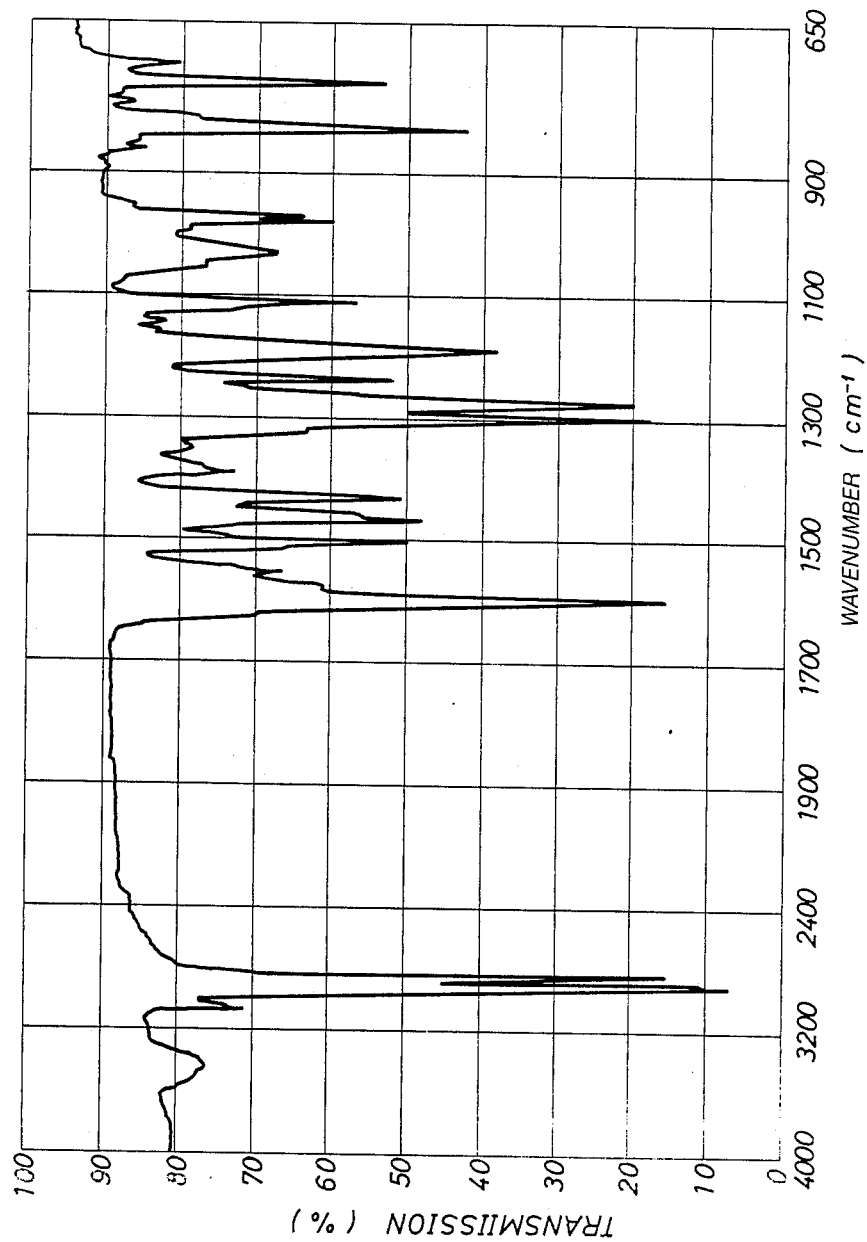
Figure 4:
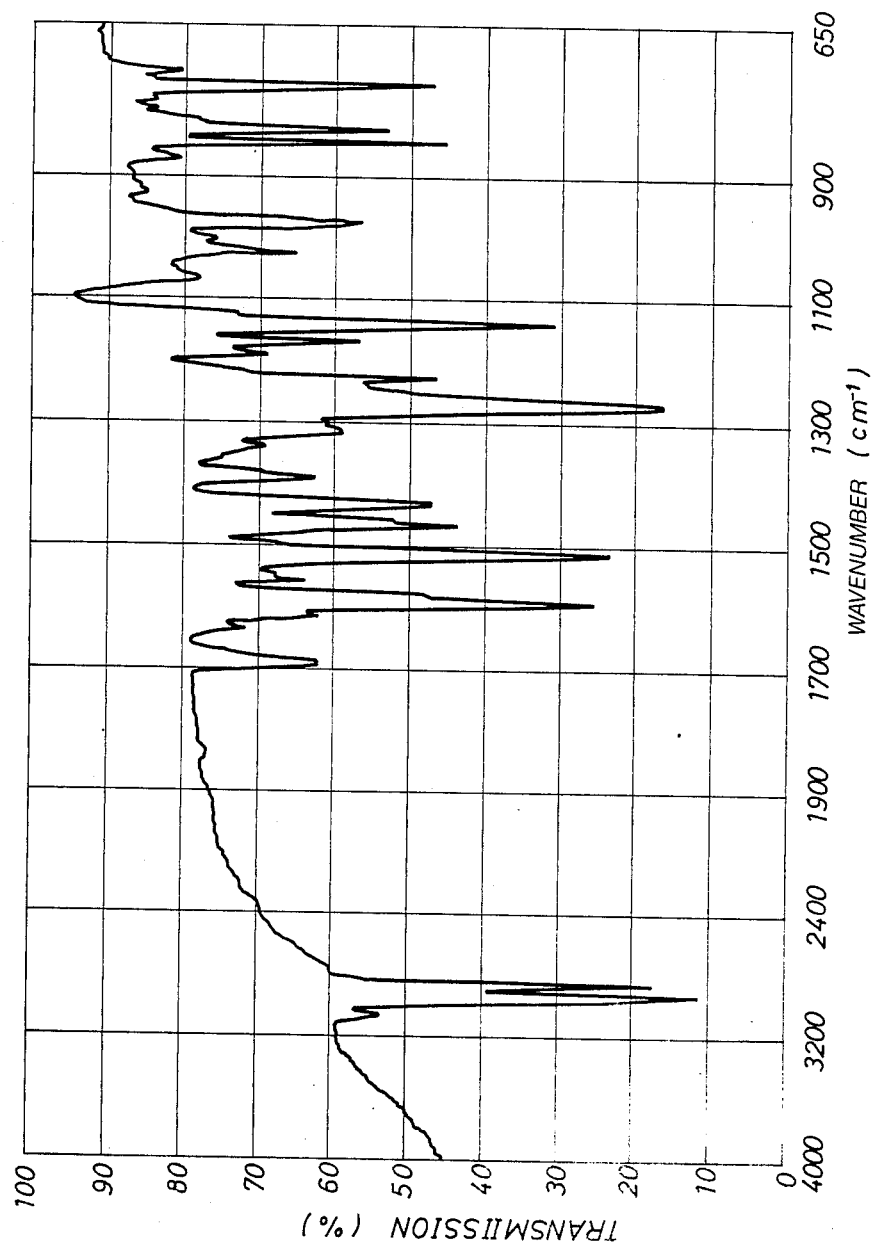

| Compound | Quinaldines | dihydroxy-benzaldehydes | halogenated hydrocarbons | Chromogenic Compounds | Property | Melting point (°C.) | I.R. |
|---|---|---|---|---|---|---|---|
| 2 | 2-methylquinoline (C₂H₅O substituent) | 2,4-dihydroxybenzaldehyde | benzyl chloride (PhCH₂Cl) | quinoline with CH=CH linkage to dibenzyloxyphenyl | Yellow color 424 nm (AcOH) 450 nm (clay) | 120~126.5 | FIG. 2 |
| 3 | 2-methylquinoline | 2,4-dihydroxybenzaldehyde | $C_{12}H_{25}Br$ | quinoline-CH=CH-phenyl(OC₁₂H₂₅)₂ | Yellow color 433 nm (AcOH) 455 nm (clay) | 50.5~52.7 | FIG. 3 |
| 4 | 6-ethoxy-2-methylquinoline | 2,4-dihydroxybenzaldehyde | $C_{12}H_{25}Br$ | 6-ethoxyquinoline-CH=CH-phenyl(OC₁₂H₂₅)₂ | Yellow color 423 nm (AcOH) | 72~78 | — |
| 5 | 6-ethoxy-2-methylquinoline | 2,4-dihydroxybenzaldehyde | benzyl chloride (PhCH₂Cl) | 6-ethoxyquinoline-CH=CH-phenyl(OCH₂Ph)₂ | Yellow color 420 nm (AcOH) | 125~132 | — |
| 6 | 2-methylquinoline | 2,4-dihydroxybenzaldehyde | $C_8H_{17}Br$ | quinoline-CH=CH-phenyl(OC₈H₁₇)₂ | Yellow color 426 nm (AcOH) | 45~53 | FIG. 4 |

TABLE 23-continued

| | | | | | |
|---|---|---|---|---|---|
| 7 | ![quinoline with Cl, CH3] | ![resorcinol-CHO] | C8H17Br | ![product with Cl, OC8H17] | Yellow color 435 nm (AcOH) 455 nm (clay) | 81~86 | — |
| 8 | ![quinoline with CH3, CH3] | ![resorcinol-CHO] | C8H17Br | ![product with CH3, OC8H17] | Yellow color 432 nm (AcOH) 451 nm (clay) | 55.5~61 | — |

| | C (%) | H (%) | N (%) |
|---|---|---|---|
| Elemental analysis of Compound No. 2 | | | |
| Calcd. for C31H25NO2: | 83.97 | 5.64 | 3.16 |
| Found: | 83.73 | 5.64 | 2.91 |
| Elemental analysis of Compound No. 3 | | | |
| Calcd. for C41H61NO2: | 82.13 | 10.18 | 2.33 |
| Found: | 81.87 | 10.33 | 2.24 |
| Elemental analysis of Compound No. 4 | | | |
| Calcd. for C43H65NO3: | 80.24 | 10.10 | 2.17 |
| Found: | 80.83 | 9.95 | 2.23 |
| Elemental analysis of Compound No. 5 | | | |
| Calcd. for C33H29NO3: | 81.31 | 5.95 | 2.87 |
| Found: | 81.05 | 5.46 | 2.77 |
| Elemental analysis of Compound No. 6 | | | |
| Calcd. for C33H45NO2: | 81.31 | 9.24 | 2.87 |
| Found: | 80.32 | 9.66 | 2.44 |
| Elemental analysis of Compound No. 7 | | | |
| Calcd. for C33H44NO2Cl: | 75.93 | 8.43 | 2.68 |
| Found: | 75.82 | 8.33 | 2.76 |
| Elemental analysis of Compound No. 8 | | | |
| Calcd. for C34H47NO2: | 81.43 | 9.38 | 2.79 |
| Found: | 80.98 | 9.42 | 2.83 |

EXAMPLE 9

Preparation of pressure-sensitive recording paper

The chromogenic compounds obtained in Examples 1 to 8 were used. For comparison, 2-(4-octyloxystyryl)-quinoline (disclosed in G.B. No.2136823A) and 2-(3-methoxy-4-dodecyloxystyryl)quinoline were used.

At first, the microencapsulation of the chromogenic compound was performed as follows:

Six parts by weight of the chromogenic compound was dissolved in 94 parts by weight of isopropylbiphenyl. Separately, 24 parts of gelatin and 24 parts of gum arabic were dissolved in 400 parts of water, and the resulting solution was adjusted to pH 7. The first solution was added to the second solution, and the mixture was emulsified with a homogenizer. To this emulsion was added 1000 parts of hot water, followed by stirring at 50° C. for 30 minutes. One part of 10 % aqueous solution of sodium hydroxide was added, followed by stirring at 50° C. for 30 minutes. Dilute acetic acid was slowly added to adjust the pH thereof to 4.5. Stirring was continued at 50° C. for about 1 hour. The emulsion was cooled to 0 to 5° C. and stirred for 30 minutes. 35 parts of 4% aqueous solution of glutaraldehyde was slowly added thereto thereby forming microcapsules. A dilute aqueous solution of sodium hydroxide was added to adjust the pH to 6. Stirring was continued at room temperature for several hours to complete microencapsulation. The microcapsule dispersion thus prepared was applied to paper, followed by drying, to obtain microcapsules coating paper (pressure-sensitive upper paper).

Each of the upper paper samples was placed on clay coating paper (pressure-sensitive lower paper), with the microcapsules and the coated clay in contact with each other. Pressure was applied to the pressure-sensitive paper by rolling to effect color formation. The color density on the lower paper was measured with a reflection densitometer. The results are shown in Table 3. To evaluate the stability to light of the chromogenic compounds, the same procedure as above was repeated after the upper paper had been exposed to sunlight for 20 minutes or 40 minutes. The results are also shown in Table 3. The data are compared in percentage in parentheses. Also, the desensitization of the chromogenic compounds were measured by the aforementioned method. The results are also shown in Table 3.

As seen from Table 3, the chromogenic compounds of the present invention are comparable with that disclosed in G.B. No. 2136823A and are superior in desensitization to that disclosed in G.B. No. 2136823A. The stability to light is greatly improved in the case of chromogenic compounds in which one of the substituent groups on the styryl group is at the ortho position, as in Examples 1, 2, 3, 7 and 8.

TABLE 3

| Chromogenic Compound | Color Density (Exposing Time) | | | Desensitization |
|---|---|---|---|---|
| | 0 min. | 20 min. | 40 min. | |
|  (Comparative Example 1) | 0.673 (100) | 0.461 (68) | 0.433 (64) | — |
|  (Comparative Example 2) | 0.747 (100) | 0.495 (66) | 0.459 (61) | 0.48 |
| 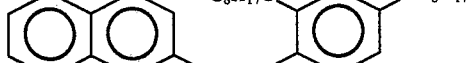 (Example 1) | 0.858 (100) | 0.749 (87) | 0.718 (84) | 0.23 |
| 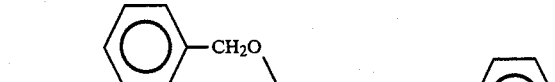 (Example 2) | 0.812 (100) | 0.690 (85) | 0.657 (81) | — |
| 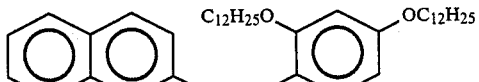 (Example 3) | 0.850 (100) | 0.756 (89) | 0.705 (83) | 0.16 |

TABLE 3-continued

| Chromogenic Compound | Color Density (Exposing Time) | | | Desensitization |
|---|---|---|---|---|
| | 0 min. | 20 min. | 40 min. | |
| (Example 4) | 0.759 (100) | 0.523 (69) | 0.493 (65) | 0.25 |
| (Example 5) | 0.734 (100) | 0.521 (71) | 0.491 (67) | — |
| (Example 6) | 0.767 (100) | 0.522 (68) | 0.483 (63) | 0.25 |
| (Example 7) | 0.811 (100) | 0.673 (83) | 0.640 (79) | 0.24 |
| (Example 8) | 0.831 (100) | 0.673 (81) | 0.631 (76) | 0.23 |

EXAMPLE 10

Preparation of Heat-Sensitive Recording Paper 30 parts by weight of 1-(2,4-benzyloxyphenyl)-2-(2'-quinolyl)ethylene (obtained in Example 2) was crushed in 150 parts by weight of 10% aqueous solution of polyvinyl alcohol and 65 parts by weight of water for 1 hour using a ball mill until the particle size was 1 to 3 μm. (The product was designated as component A.) Separately, 35 parts by weight of bisphenol A was crushed in 150 parts by weight of 10 % aqueous solution of polyvinyl alcohol and 65 parts by weight of water using a ball mill until the particle size was 1 to 3 μm. (The product was designated as component B.) 3 parts by weight of component A and 67 parts by weight of component B were mixed and the resulting mixture was applied to base paper at a coating weight of about 5 g/m². The resulting heat-sensitive paper rapidly formed a yellow color upon heating with a thermal pen. The color image was stable to light and resistant to moisture.

What is claimed is:

1. A chromogenic compound represented by the formula (I):

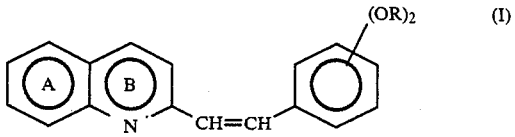

wherein R represents an alkyl group of 6 to 12 carbon atoms or benzyl group, and ring A and ring B in the quinolyl group may be substituted by a chlorine atom, a methyl group or an ethoxy group.

2. A chromogenic compound according to claim 1, which is 1-(2,4-dioctyloxyphenyl)-2-(2'-quinolyl)ethylene,
1-(2,4-dibenzyloxyphenyl)-2-(2'-quinolyl)ethylene,
1-(2,4-didodecyloxyphenyl)-2-(2'-quinolyl)ethylene,
1-(4,5-didodecyloxyphenyl)-2-(6'-ethoxy-2'-quinolyl)ethylene,
1-(4,5-dibenzyloxyphenyl)-2-(6'-ethoxy-2'-quinolyl)ethylene,
1-(5,6-dioctyloxyphenyl)-2-(2'-quinolyl)ethylene,
1-(2,4-dioctyloxyphenyl)-2-(6'-chloro-2'-quinolyl)ethylene, or
1-(2,4-dioctyloxyphenyl)-2-(6'-methyl-2-quinolyl)ethylene.

* * * * *